United States Patent [19]

Dzwonczyk et al.

[11] Patent Number: 5,454,377
[45] Date of Patent: Oct. 3, 1995

[54] METHOD FOR MEASURING THE MYOCARDIAL ELECTRICAL IMPEDANCE SPECTRUM

[75] Inventors: Roger R. Dzwonczyk, Columbus, Ohio; Alan Y. Liu, Basking Ridge, N.J.; Alan W. Hartzler, Columbus, Ohio

[73] Assignee: The Ohio State University, Columbus, Ohio

[21] Appl. No.: 134,288

[22] Filed: Oct. 8, 1993

[51] Int. Cl.[6] ................................................ A61B 5/05
[52] U.S. Cl. ................................................ 128/734
[58] Field of Search ............................. 128/734; 607/17, 607/24

[56] References Cited

U.S. PATENT DOCUMENTS

| | | |
|---|---|---|
| 4,805,621 | 2/1989 | Heinze et al. |
| 4,823,797 | 4/1989 | Heinze et al. |
| 4,870,967 | 10/1989 | Hanze et al. ........................ 128/734 |
| 4,899,750 | 2/1990 | Ekwall . |
| 5,051,352 | 9/1991 | Martindale et al. . |
| 5,203,344 | 4/1993 | Scheltinga et al. ................ 128/734 |

OTHER PUBLICATIONS

Ozwonczyk et al., "A New Apparatus and Method for Measuring the Myocardial Electrical Impedance Spectrum," OSU Hospitals.
Garrido et al., "Bioelectrical Tissue Resistance During Various Methods of Myocardial Preservation", Ann Thorac Surg. vol. 36, No. 2, Aug. 1983, pp. 143–151.
Ellenby et al., "On–line Detection of Reversible Myocardial Ischemic Injury by Measurement of Myocardial Electrical Impedance", Ann Thorac Surg, vol. 44, No. 6, Dec. 1987, pp. 587–597.
Geddes et al., Principles of Applied Biomedical Instrumentation, John Wiley & Sons, New York, 1989, Chap. 11, "Detection of Physio–logical Events by Impedance", pp. 537–545.
Dzwonczyk et al., "A New Apparatus and Method for Measuring the Myocardial Electrical Impdance Specturm", 1992 Computers in Cardiology, 1992, p. 162.
Yun et al., "Alterations in Left Ventricular Diastolic Twist Mechanics During Acute Human Cardiac Allograft Rejection", Circulation, vol. 83, No. 3, Mar. 1991, pp. 962–973.
Howie et al., "The Use of Myocardial Tissue Impedance to Determine Esmolol's Effectiveness to Protect Against Ischaemia", Anesthesiology vol. 75, No. 3A, Sept. 1991, pp. 104–A443.
Romanelli, et al., "Impedance as an Early Marker for Myocardial Ischemia", Anesthesiology, vol. 73, No. 3A, Sept. 1990, A482.
Howie et al., "The Effect of Isoproterenol on Myocardial Ischemia Using Impedance as an Indicator", Anesth Analg, vol. 72, 1991, S115.
Jones et al., "The Measurement of the Conductance of Electrolytes I. An Experimental and Theoretical Study of Principles of Design of the Wheatstone Bridge for Use with Alternating Currents and an Improved Form of Direct Reading Alternating Current Bridge", J. Am. Chem. Soc. vol. 50, Apr. 1928, pp. 1049–1092.

Primary Examiner—Lee S. Cohen
Assistant Examiner—Robert L. Nassol, Jr.
Attorney, Agent, or Firm—Frank H. Foster

[57] ABSTRACT

A method for measuring the complex impedance spectrum of a portion of the myocardium by placing two electrodes on a portion of the myocardium and applying a current pulse to the electrodes to generate a voltage response between the electrodes. Both the current pulse and voltage response are sampled and digitized and then a Fast fourier transform is taken of both the current pulse and the voltage response to obtain a complex current pulse spectrum and a complex voltage response spectrum. Next, the complex voltage response spectrum is divided by the complex current pulse spectrum to obtain the complex impedance spectrum.

6 Claims, 5 Drawing Sheets

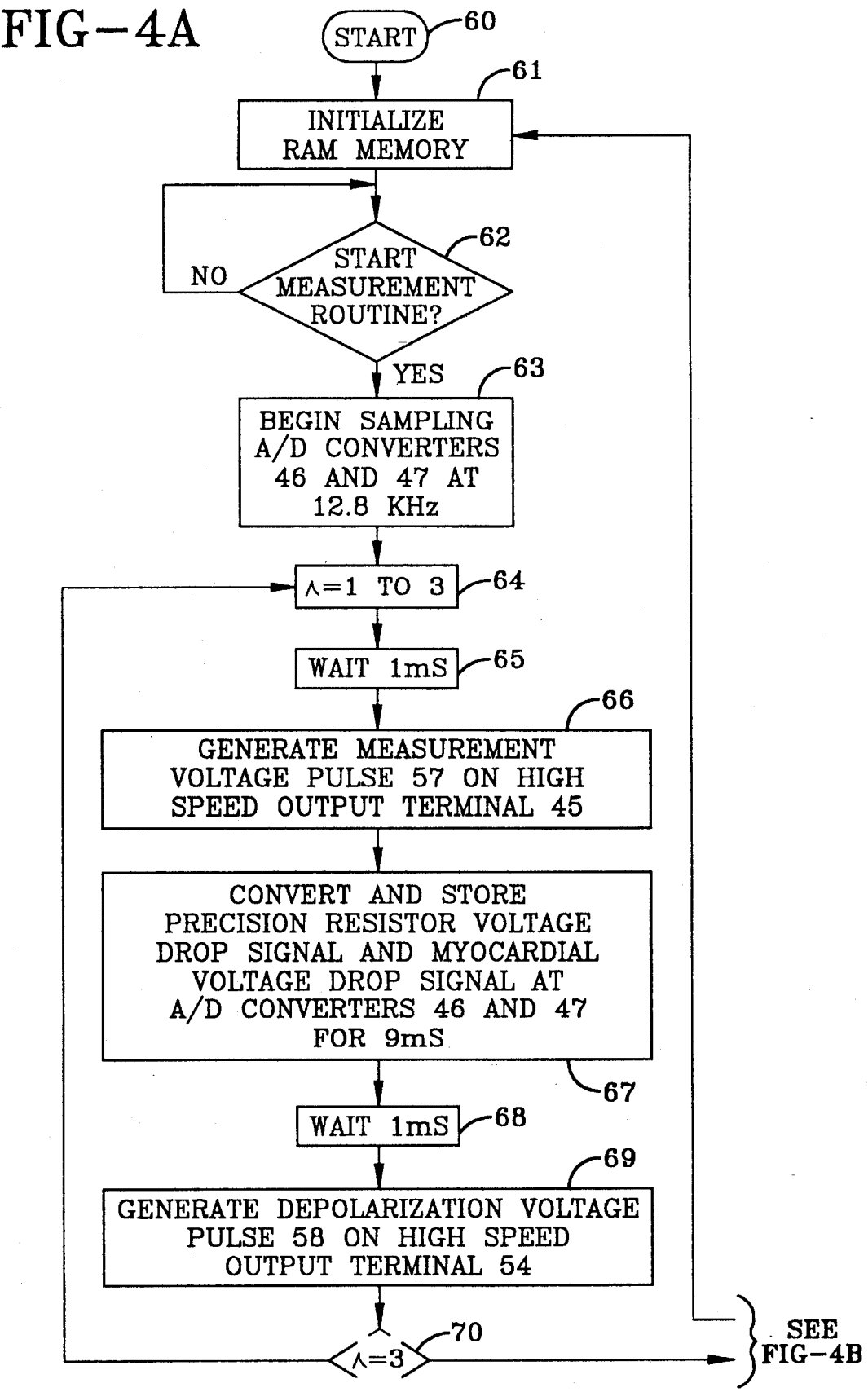

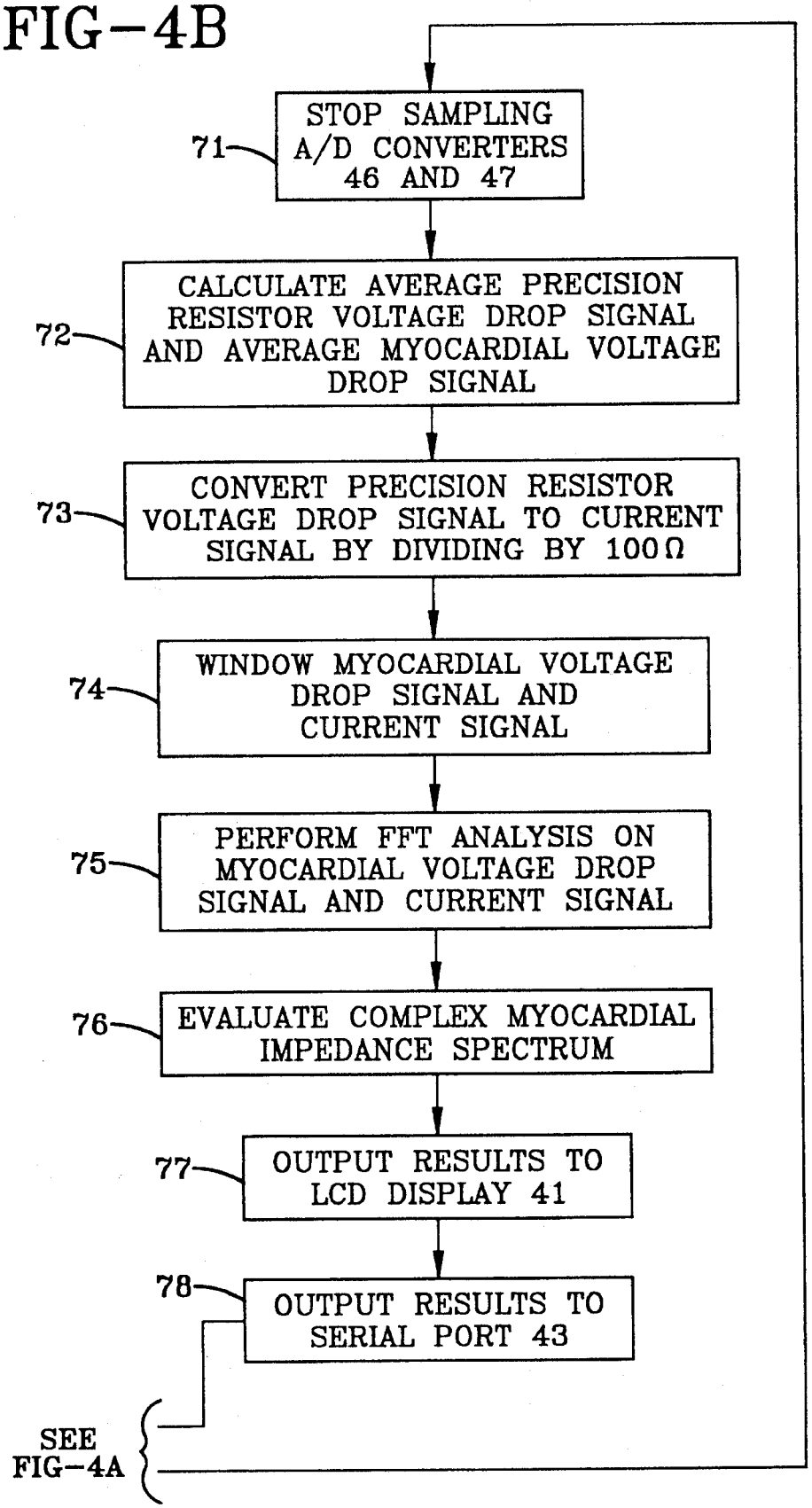

METHOD FOR MEASURING THE MYOCARDIAL ELECTRICAL IMPEDANCE SPECTRUM

TECHNICAL FIELD

This invention relates generally to electronic apparatus for medical testing, and more particularly relates to an apparatus and method for detecting or monitoring the condition of the myocardium.

BACKGROUND ART

Myocardial electrical impedance is correlated to the vitality of the myocardial tissue. It is well established in the literature that myocardial impedance increases by as much as 200 percent of baseline value with regional and global ischemia, edema, pathologic tissue ultrastructural changes ATP depletion and lactate accumulation. When these pathophysiologic conditions are reversed before permanent tissue damage is incurred, the myocardial electrical impedance returns to baseline values. The exact etiology of these electrical impedance changes is unknown.

Myocardial electrical impedance has both a resistive and a capacitive reactive component. It has been shown that the phase angle between the real and imaginary part of the myocardial electrical impedance at a frequency of 5 KHz and, to a lesser extent, the real part of the myocardial electrical impedance at 200 Hz exhibit a specific characteristic rise during ischemia.

The literature clearly indicates that myocardial electrical impedance has value as a diagnostic tool. Myocardial electrical impedance can identify severe but reversible ischemic injury. The variable has potential use in measuring the viability of the myocardium during cardioplegia and determining the need for and type of resuscitation following coronary artery bypass graft surgery.

It is hypothesized that myocardial electrical impedance may also be useful in diagnosing tissue rejection by the immune system following cardiac transplant surgery. Cardiac tissue rejection results in myocardial edema and other conditions that have previously been shown to affect cardiac tissue impedance. Currently, the condition of the transplanted cardiac tissue is monitored by routine histopathologic biopsies taken from the endocardium. The results from this procedure often take a day to obtain whereas myocardial electrical impedance can be measured in a matter of minutes. The potential benefit of using myocardial impedance rather than histopathologic biopsies is that tissue rejection could be diagnosed and treated much earlier which may result in reversing the rejection process and preserving the transplanted heart.

Myocardial electrical impedance has been measured between 0 and 10 KHz using techniques requiring both two and four electrodes to be attached to the heart tissue. One two-electrode technique, demonstrated for instance by Jones et al. (1928), employs a Wheatstone bridge network consisting of four impedances connected in a circular series configuration. Two of the impedances are discrete components of known fixed value. The third impedance is typically composed of a discrete calibrated variable resistor and capacitor connected in parallel. The fourth impedance is the tissue to be measured and is connected to the Wheatstone bridge via the two electrodes. A direct current or sinusoidal alternating current signal generator at a given desired frequency is connected to opposite corners of the bridge and a detector such as headphones or an oscilloscope connected to the opposing corners of the bridge. The impedance of the tissue is determined by adjusting the variable resistor and capacitor to achieve a null in the detector and then reading the values of resistance and capacitance from the calibrated components.

Another two-electrode technique, referred to by Garrido et al. (1983) and called a myocardial electrical impedance meter, apparently measures myocardial electrical impedance at one specific frequency. That frequency may be 0 Hz.

The four-electrode technique has been the method most often used to measure tissue impedance in the recent research literature. This technique, described for instance by Ellenby et al. (1987), employs a linear array of four equally spaced electrodes attached to the myocardial tissue. A known electrical current is impressed between the outer two electrodes and the resulting voltage drop is measured between the inner electrodes. The tissue impedance is calculated from Ohm's Law by dividing the voltage by the current. This technique has been used to measure tissue impedance at frequencies between 0 and 10 KHz. The frequency at which the impedance is measured is determined by the frequency of the impressed current signal. This method has been used to extract the resistive and capacitive reactive components of the impedance as well as the phase of the impedance at a given frequency.

These past techniques for measuring myocardial electrical impedance have several disadvantages which make them impractical for clinical use. The two-electrode techniques cause electrode-tissue polarization. This phenomenon has been shown to cause drift and general inaccuracy in the electrical impedance measurement. The four-electrode technique requires that a more complicated, less clinically feasible electrode montage be placed on the myocardium in order to perform the measurement. Finally, none of these previous techniques generates an electrical impedance spectrum, but rather only generates an impedance at one particularly frequency.

In view of past research in myocardial electrical impedance and the potential clinical utility of myocardial impedance it is an object of the invention to provide a myocardial electrical impedance spectrometer having the following ideal design objectives: a) the spectrometer should determine myocardial tissue electrical impedance over a certain frequency range of interest rather than simply a meter which measures impedance at one particular frequency since conditions such as ischemia produce characteristic complex impedance changes at specific frequencies; b) the apparatus should evaluate the complex electrical impedance rather than just the modulus or magnitude of the impedance since the phase angle of the impedance at certain frequencies has shown to have characteristic changes with ischemia; c) the apparatus should evaluate the myocardial electrical impedance spectrum in a relatively short period of time in order to promote early diagnosis and early effective treatment of pathologic heart conditions; and d) the apparatus should have an uncomplicated electrode interface with the heart and, where possible, make use of a preexisting electrode interface.

BRIEF DESCRIPTION OF INVENTION

The method of the present invention is a method for measuring the complex impedance spectrum of the portion of the myocardium between two electrodes. A current pulse is applied to the electrodes and through the interposed myocardium to generate a voltage response between the electrodes. Both the applied current pulse and the voltage response are sampled and digitized. A fast Fourier transform is performed upon both the digitized current pulse and the digitized voltage response to obtain a complex, current pulse spectrum and a complex voltage response spectrum. In other words, both the current pulse and the voltage response pulse are converted from the time domain to the frequency domain by means of a Fourier transformation performed by a computer algorithm. The result of this transform is a set of data for the current pulse which consists of a current amplitude and phase for each of a plurality of frequencies and also a set of data for the voltage pulse, which consists of an amplitude and phase angle for each of the same plurality of frequencies. The complex voltage response component for each frequency in the voltage response spectrum is divided by the complex current pulse component for each corresponding frequency in the current pulse spectrum to obtain a complex impedance spectrum. The complex impedance spectrum comprises a set of data which has an impedance amplitude and phase angle for each of the plurality of frequencies. The complex impedance spectrum may then be displayed for interpretation by a physician and/or may be further mathematically manipulated by other algorithms to display additional data. The display of the complex impedance spectrum may, for example, be a plot of the amplitude for each frequency component plotted as a function of frequency, and may also include a display of the phase for each frequency component plotted as a function of frequency.

The apparatus for measuring the complex impedance spectrum of a portion of a myocardium between two electrodes has a current source pulse generator connected in series to a resistor and the electrodes. First amplifier circuitry has its input connected to the resistor for inputting the voltage across the resistor and outputting a signal representing the current pulse from the pulse generator. Second amplifier circuitry has its input connected across the electrodes for inputting the voltage response across the electrodes in response to the current pulse and outputting a signal representing the voltage response at said electrodes. A different analog to digital converter is connected to the output of each amplifier circuit. An electronic, digital computer circuit is connected to receive the outputs from both analog to digital converters and perform the fast Fourier transform algorithm upon those outputs to generate data representing the impedance of the myocardium between the electrodes as a function of frequency.

BRIEF DESCRIPTION OF DRAWINGS

FIG. 4 is a flow chart diagram illustrating the operation of the micro controller software embodying the present invention.

Figure 1:
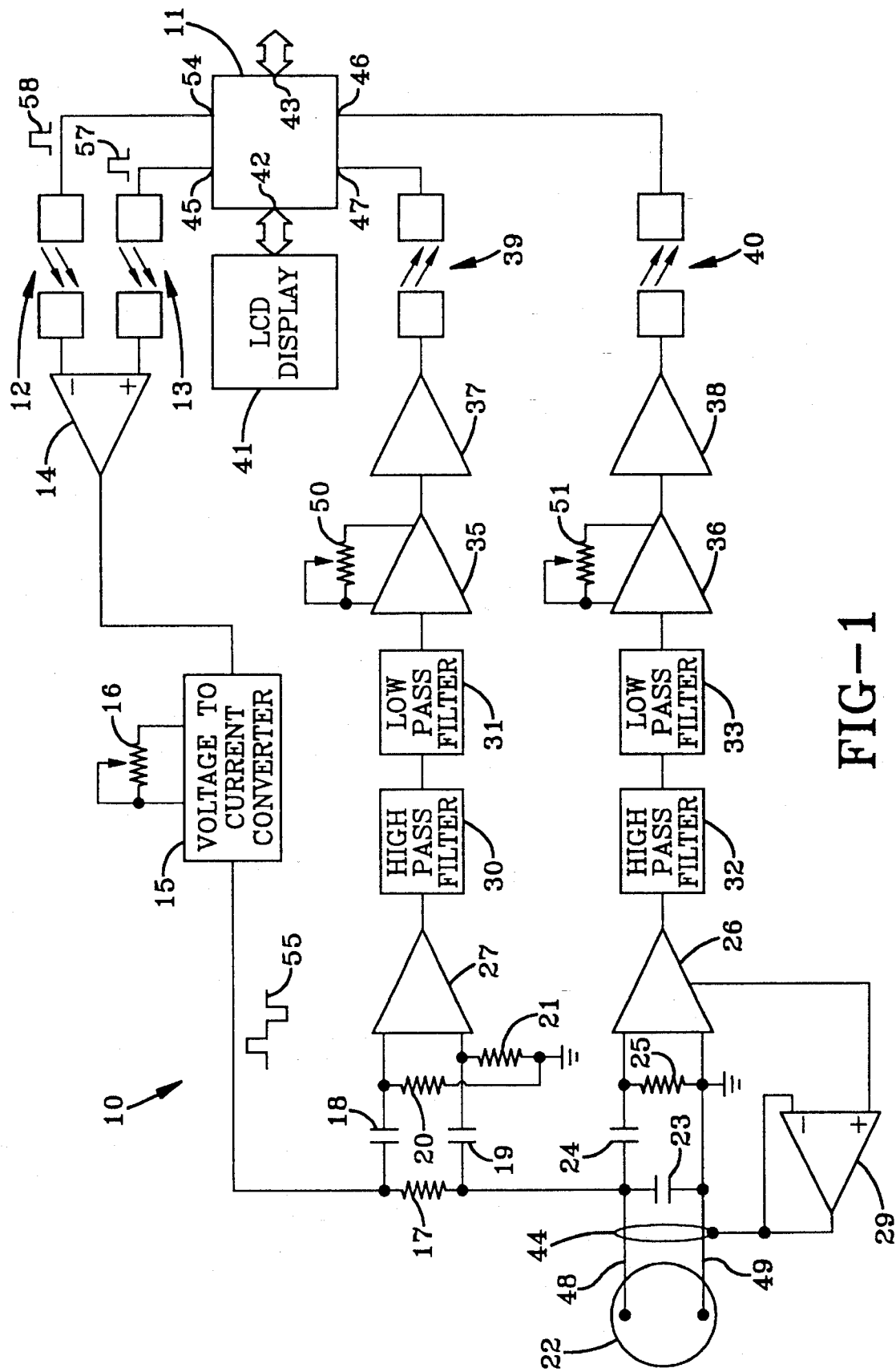
FIG. 1 is a schematic diagram illustrating the apparatus of the preferred embodiment of the invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art.

DETAILED DESCRIPTION

The apparatus of the invention measures the complex electrical impedance spectrum of the myocardium (heart muscle) between the frequencies of 270 Hz and 5.9 KHz at 100 Hz intervals. The apparatus is designed around an Intel 80C196 microcontroller. The analog circuitry is used to filter and apply a stimulus signal to the myocardium and measure, filter and amplify the resultant voltage response signal. Connection to the myocardium is made via two standard commercially available electrodes which are ordinarily used for connecting a pacemaker to the heart.

The apparatus obtains an impedance spectrum in the following way: A current pulse is sent to the electrodes and the resultant voltage response across the electrodes is measured. Both the current pulse and voltage response are processed by the analog circuit and digitized by the analog-to-digital converter of the microcontroller. The microcontroller performs a fast Fourier transform on the current pulse and voltage response in order to transform each signal from the time domain to the complex frequency domain. Following this transformation, the microcontroller serially downloads the two complex signals to a standard microcomputer for further processing.

The microcomputer divides each complex frequency component of the voltage response by the associated component of the current pulse, thereby producing the complex impedance spectrum of the volume of myocardial tissue between the pacing electrodes. The microcomputer calculates the magnitude of the complex impedance and plots this magnitude versus frequency. This plot represents the impedance spectrum of the tissue. The microcomputer also reports the average impedance magnitude of the impedance spectrum. The entire process is repeated automatically every 10 milliseconds. All data is stored in an unreduced format for subsequent analysis. This technique allows for extracting the capacitive reactive, inductive reactive and resistive components of the impedance as well as the phase of the impedance at any frequency in the impedance spectrum.

The preferred embodiment of the apparatus 10 shown in FIG. 1 includes a microcontroller 11, preferably in Intel 80C196, having a central processing unit (CPU), random access memory (RAM), erasable programmable read-only memory (EPROM), at least two analog-to-digital converters (ADCs) 46 and 47, at least one parallel input/output (I/O) port 42, at least two high speed output terminals 45 & 54, and at least one serial I/O port 43. Parallel port 42 interfaces with the liquid crystal display 41 which displays the myocardial impedance spectrum and measurements made by apparatus 10. Serial port 43 may be interfaced with the serial port of another computer, not part of the present invention, so that measurements made by apparatus 10 can be downloaded for data storage and further processing, if desired.

High speed output terminals 45 and 54 of the microcontroller 11 are connected to the two optocouplers 13 and 12, respectively. The voltage output of the optocoupler 12 is connected to the inverting input of bipolar amplifier circuit 14. Similarly, the voltage output of optocoupler 13 is connected to the noninverting input of bipolar amplifier circuit 14. The voltage output of bipolar amplifier circuit 14 is connected to the input of the voltage-to-current converter circuit 15. The magnitude of the current output from the voltage-to-current converter circuit 15 can be adjusted by the current adjust resistor 16. The current output of the voltage-to-current converter circuit 15 is connected to precision resistor 17 which, in turn, is connected to the myocardium 22 via pacing lead 48. Pacing lead 49 provides a return connection from the myocardium 22 to ground.

The two terminals of precision resistor 17 are connected, one each, to coupling capacitors 18 and 19 which are, in turn, connected, one each, to resistors 20 and 21 and, one each, to the inputs of instrumentation amplifier 27. The other terminal of resistors 20 and 21 is connected to ground.

The output of instrumentation amplifier 27 is connected to the input of highpass filter circuit 30. The output of highpass filter circuit 30 is connected to the input of the lowpass filter circuit 31. The output of lowpass filter circuit 31 is connected to the input of gain amplifier circuit 35. The gain of gain amplifier circuit 35 may be adjusted by gain resistor 50. The output of gain amplifier circuit 35 is connected to voltage level shifting circuit 37. The output of the voltage level shifting circuit 37 is connected to the input of optocoupler 39. Finally, the output of optocoupler 39 is connected to A/D converter 47 on the microcontroller 11.

The proximal end of pacing lead 48 is connected to one terminal of compensating capacitor 23 and one terminal of coupling capacitor 24. The other terminal of coupling capacitor 24 is connected to one terminal of resistor 25 and one input of instrumentation amplifier 26. The proximal terminal of pacing lead 49 is connected to the other terminal of compensating capacitor 23, resistor 25 and the other input of instrumentation amplifier 26. The shield driver output of instrumentation amplifier 26 is connected to the input of shield driver amplifier circuit 29. The output of shield driver amplifier circuit 29 is connected to the shield 44 surrounding pacing leads 48 and 49.

The output of instrumentation amplifier 26 is connected to the input of highpass filter circuit 32. The output of highpass filter circuit 32 is connected to the input of the lowpass filter circuit 33. The output of lowpass filter circuit 33 is connected to the input of gain amplifier circuit 36. The filter circuits form a bandpass filter confining the signals to the frequencies of interest in a band extending from 270 Hz to 5.9 KHz in the preferred embodiment. The gain of gain amplifier circuit 35 may be adjusted by gain resistor 51. The output of gain amplifier circuit 36 is connected to the input of voltage level shifting circuit 38. The output of the voltage level shifting circuit 38 is connected to the input of optocoupler 40. Finally, the output of optocoupler 40 is connected to A/D converter 46 on the microcontroller 11.

Figure 2:
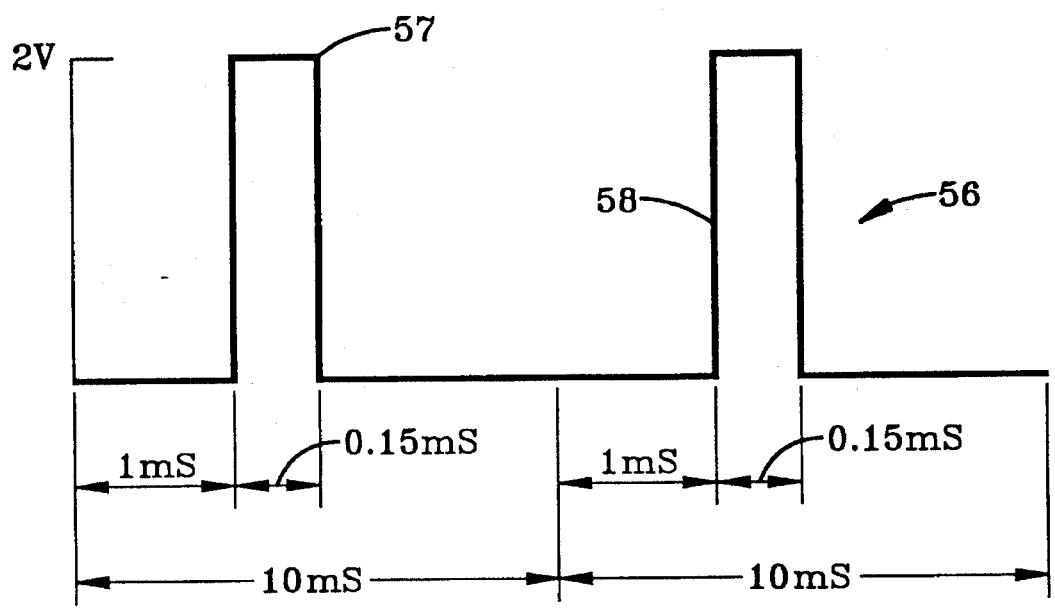
FIG. 2 and FIG. 3 are electrical oscillograms illustrating circuit signals.

The preferred embodiment of the voltage excitation signal 56 shown in FIG. 2 consists of a measurement voltage pulse 57 and a depolarization voltage pulse 58. Both voltage pulses are +2 V in magnitude and 0.15 mS in duration and approximate the shape of rectangular waves. The voltage pulses are separated by a 10 mS quiescent time interval. Microcontroller 11, FIG. 1, generates the measurement voltage pulse 57 on high speed output terminal 45, FIG. 1, and generates the depolarization voltage pulse 58, on high speed output terminal 54, FIG. 1.

Figure 3:
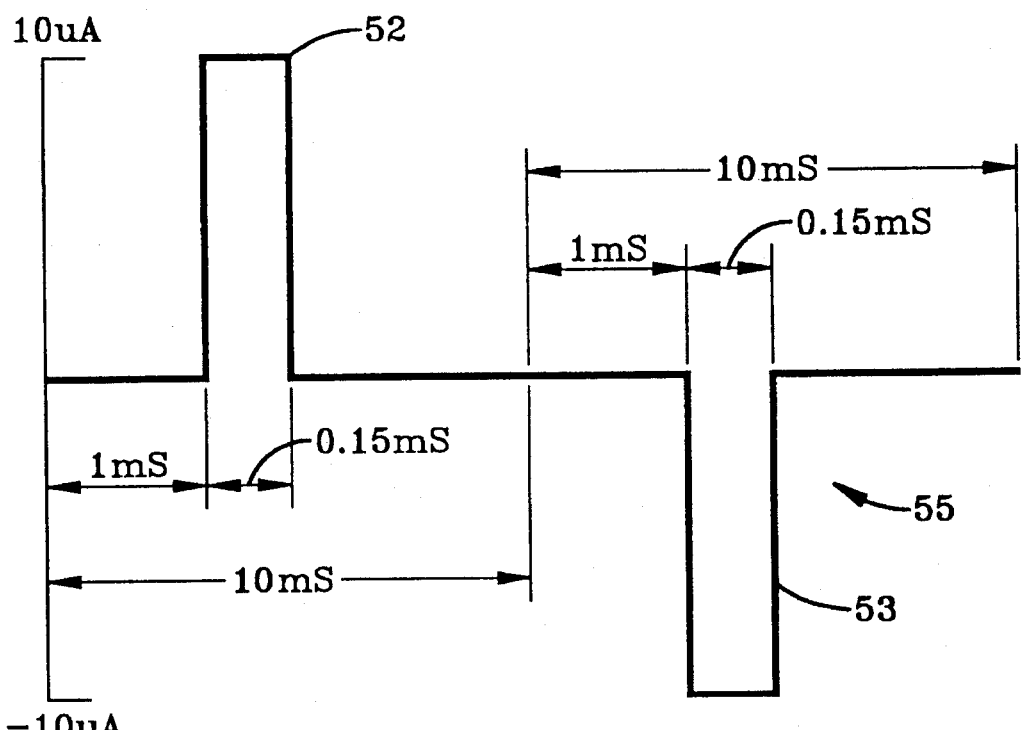

As a result of the microcontroller 11 generating the voltage excitation signal 56, FIG. 2, and the action of the optocouplers 12 and 13, bipolar amplifier circuit 14, voltage-to-current converter circuit 15 and current adjust resistor 16, FIG. 1, the current excitation signal 55 shown in FIG. 3 is produced at the output of the voltage-to-current converter circuit 16. The preferred embodiment of the current excitation signal 55 used to evaluate the myocardial electrical impedance spectrum and shown in FIG. 3, consists of a positive measurement current pulse 52 and a negative depolarization current pulse 53. Both current pulses have an absolute magnitude of 10 µA and are 0.15 mS in duration and approximate the shape of rectangular waves. The current pulses are separated by a 10 mS quiescent time interval.

OPERATION OF THE PREFERRED APPARATUS

The operation of apparatus 10, FIG. 1, proceeds as follows. Microcontroller 11 generates the measurement voltage pulse 57 at the high speed output terminal 45. This voltage pulse is coupled to the noninverting terminal of the bipolar amplifier circuit 14 and passed on to the input of the voltage-to-current converter circuit 15 as a positive voltage pulse. This voltage pulse is converted to the positive 10 µA measurement current pulse 52 by the action of the voltage-to-current converter circuit 15 and the current adjust resistor 16. The measurement current pulse 52 passes through precision resistor 17, pacing lead 48, myocardium 22 and pacing lead 49 to ground. The voltage drop across precision resistor 17, which is produced by and proportional to the measurement current pulse 52, is inputted to instrumentation amplifier 27. Coupling capacitor 18 in combination with resistor 20 and coupling capacitor 19 in combination with resistor 21 form two analog highpass filters that couple the alternating current component of the precision resistor voltage drop signal generated across precision resistor 17 to instrumentation amplifier 27 while blocking any direct current signal component. The precision resistor voltage drop signal outputted from the instrumentation amplifier 27 is filtered by the highpass filter circuit 30 at a cutoff frequency of 270 Hz and the lowpass filter circuit 31 at a cutoff frequency of 5.9 Hz and amplified by gain amplifier circuit 35 in conjunction with gain resistor 50. The precision resistor voltage drop signal is then level shifted by the voltage level shift circuit 37 so that the voltage drop signal is entirely positive with respect to ground. The shifted precision resistor voltage drop signal is then inputted to A/D converter 47 through optocoupler 39.

The voltage drop across the myocardium 22, which is produced by the measurement current pulse 52, is inputted to instrumentation amplifier 26. Coupling capacitor 24 in combination with resistor 25 form an analog highpass filter which couple the alternating current component of the myocardial voltage drop signal generated across the myocardium 22 to instrumentation amplifier 26 while blocking any direct current signal component. The myocardial voltage drop signal outputted from instrumentation amplifier 26 is filtered by the highpass filter circuit 32 at a cutoff frequency of 270 Hz and the lowpass filter circuit 33 at a cutoff frequency of 5.9 Hz and amplified by gain amplifier circuit 36 in conjunction with gain resistor 51. The myocardial voltage drop signal is then level shifted by the voltage level shift circuit 38 so that the voltage drop signal is entirely positive with respect to ground. The shifted myocardial voltage drop signal is then inputted to A/D converter 46 through optocoupler 40.

Following the 10 mS quiescent time interval after generating the measurement voltage pulse 57, microcontroller 11 generates the depolarization voltage pulse 58 at the high speed output terminal 54. This voltage pulse is coupled to the inverting terminal of the bipolar amplifier circuit 14 and passed on to the input of the voltage-to-current converter circuit 15 as a negative voltage pulse. This voltage pulse is converted to the negative 10 μA depolarization current pulse 53 by the action of the voltage-to-current converter circuit 15 and the current adjust resistor 16. The depolarization current pulse 53 passes through precision resistor 17, pacing lead 48, myocardium 22 and pacing lead 49 to ground. This depolarization current pulse 53 effectively depolarizes the electrode-myocardium interface that had been polarized as a result of the effect of the measurement current pulse 52. Although this depolarization current pulse 53 generates a precision resistor voltage drop and myocardial voltage drop and these voltage drops will pass to the microcontroller 11 in a similar manner as those voltage drops generated by the measurement current pulse 52, they are not processed by the microcontroller 11.

The instrumentation amplifier 26, preferably an analog device AD524, as part of its operation, generates a shield drive signal which is proportional to the differential phase shift caused by stray capacitance and pacing lead cable capacitance. This shield drive signal is fed to the shield drive amplifier circuit 29 and on to the shield 44 thereby reducing or eliminating differential phase shift and improving common mode rejection. It should be pointed out that this mechanism is not part of the present invention put rather is used as standard procedure when employing instrumentation amplifiers in the way of this apparatus.

OPERATION OF THE MICROCONTROLLER

Figure 5:
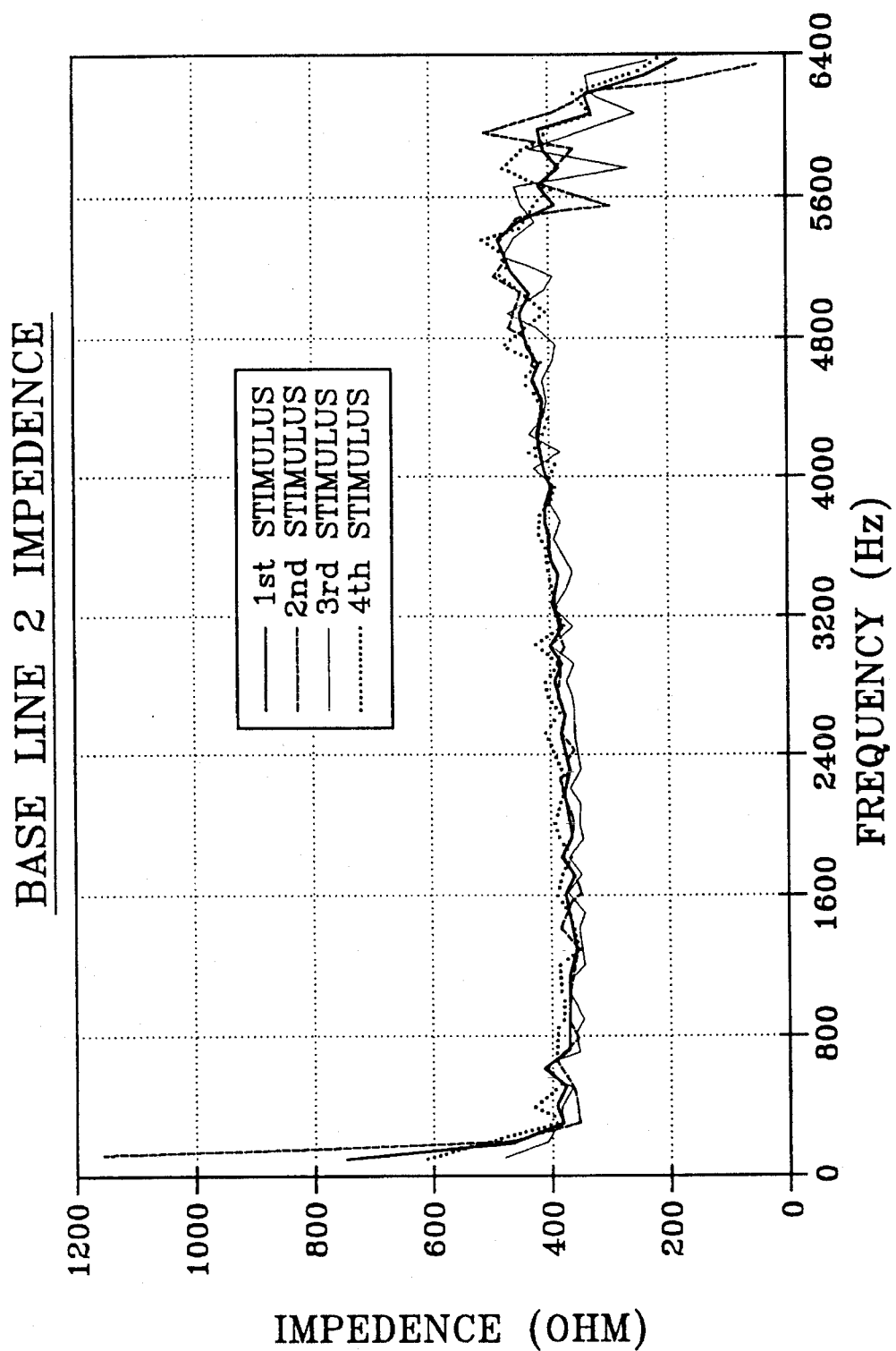
FIG. 5 is a representative graphical display of output data showing the modulus of the myocardial electrical impedance spectra from a series of successive measurements.

Referring to FIG. 4, the algorithm stored in EPROM on the microcontroller 11 proceeds as follows. When the apparatus is first powered up (60), the microcontroller 11 initializes the RAM memory (61) and waits for a command to start the measurement routine (62). This command may come from a number of sources including from a computer connected the serial port 43 of the microcontroller 11. Once the command to begin the measurement routine has been received, the microcontroller 11 begins sampling A/D converters 46 and 47 at a preferred rate of 12.8 KHz per converter (63). The microcontroller 11 then sets up a X3 repeat sequence (64). During each repeat cycle, it waits 1 mS (65) and then generates the measurement voltage pulse 57 at the high speed output terminal 45 (66). The microcontroller 11 converts and stores the voltage measurement drop signals at A/D converters 46 and 47 for a total of 10 mS (67) which includes the 1 mS wait period (65). The microcontroller 11 then waits 1 mS (68) and then generates the depolarization voltage pulse 58 at the high speed output terminal 54 (69). The microcontroller 11 checks to see if three repeat cycles have been completed (70). If not, the microcontroller 11 repeats steps 64 through 70. If three cycles have been completed, the microcontroller 11 stops sampling A/D converters 46 and 47 (71), calculates the average precision resistor voltage drop signal and average myocardial voltage drop signal (72) and then converts the average precision voltage drop signal into a current by dividing the signal by 100 Ohm (73), the value of the precision resistor 17. The myocardial voltage drop signal and current signal are multiplied by a signal processing window function (74) in preparation for fast Fourier transform analyses (75) which converts the time-domain myocardial voltage drop signal and current signal into the frequency domain. These analyses produce a complex myocardial voltage drop frequency spectrum and a complex current frequency spectrum with components at 100 Hz intervals. The microcontroller 11 evaluates the complex myocardial impedance spectrum by dividing component by component the complex myocardial voltage drop frequency spectrum by the corresponding current frequency spectrum (76). Certain results of this entire measurement process are outputted to LCD display 41 (77) as well as output to serial port 43 (78). These results may include for instance: a) the time-domain average myocardial voltage drop and current signals; b) the complex frequency-domain myocardial voltage drop, current and myocardial electrical impedance spectra; c) the average spectral myocardial electrical impedance; d) the modulus and phase of the myocardial electrical impedance at a number of particular frequencies of interests. FIG. 5 illustrates one particular output format, showing the modulus of the myocardial electrical impedance spectra resulting from a series of successive measurements. The microcontroller 11 initializes the RAM memory (61) and waits for a command to repeat the measurement routine (62).

ADVANTAGES OF THE PRESENT INVENTION

The advantages of the embodiment of FIGS. 1 through 4 can be appreciated by keeping in mind the ideal design objectives of a myocardial electrical impedance spectrometer, set forth above. The present apparatus and method evaluates the complex myocardial impedance spectrum in less than one minute. It does not compress the data in any way but retains and downloads both the time- and frequency-domain myocardial voltage drop and current data as well as the complex myocardial impedance spectral data. Therefore, the characteristic phase and modulus effects of for instance ischemia at various frequencies of interest can be charted and trended over time for diagnostic purposes. The apparatus uses standard myocardial pacing electrodes to interface with the heart without requiring modification. Two pacing electrodes are nearly always attached to the myocardium following coronary artery bypass graft and heart transplant surgery. Their proximal ends are brought out to the exterior of the body to be used for pacing the heart in the treatment of arrythmias and other pathologic heart conditions. The method of the present invention provides a means to counteract the effects of electrode-tissue polarization by impressing a depolarization pulse across the electrode-tissue interfaces. That process in combination with the process of capacitively coupling the myocardial voltage drop signal to the apparatus has shown to virtually eliminate the problems associated with polarization.

While in the foregoing an embodiment of the present apparatus and method has been disclosed in considerable detail, it is believed by those skilled in the art that many of these details may be varied without departing from the spirit of the invention. For instance, although the invention has been described as a myocardial electrical impedance spectrometer, the invention will work equally well with other tissues such as kidney, liver, pancreas and lung, to list only a few. It is quite reasonable to expect that the invention will provided diagnostic information about tissue rejection and other pathologic conditions in a timely manner which will permit early treatment and the improved likelihood of rejection reversal and tissue preservation.

In the preferred embodiment described above several electronic components, namely the instrumentation amplifiers 26 and 27 and the microcontroller 11 have been device specified. Clearly, devices which have similar operating characteristics as the device specified components may be substituted with the expectation that the invention will operate in the described way. Finally, the algorithm used to evaluate the myocardial electrical impedance spectrum may be modified in a variety of ways, while still utilizing the frequency-domain representation of signals, without departing from the spirit of the methodology.

We claim:

1. A method for measuring a complex impedance spectrum of a portion of myocardium between two electrodes, the method comprising:
   (a) applying a current pulse to the electrodes to generate a voltage response between the electrodes;
   (b) sampling and digitizing both the applied current pulse and the voltage response;
   (c) performing a fast Fourier transform upon both the digitized current pulse and the digitized voltage response to obtain a complex current pulse spectrum and a complex voltage response spectrum;
   (d) dividing the complex voltage response component for each frequency in the voltage response spectrum by the complex current pulse component for each corresponding frequency in the current pulse spectrum to obtain the complex impedance spectrum; and
   (e) displaying complex impedance spectrum data for analysis for a physician.

2. A method in accordance with claim 1 wherein said displaying step further comprises displaying the absolute value of a complex magnitude component for each of a plurality of frequency components of the complex impedance spectrum.

3. A method in accordance with claim 2 including displaying the absolute values of the magnitude component for each of a plurality of frequency components of the complex impedance spectrum as a function of frequency.

4. A method in accordance with claim 1 wherein said displaying step further comprises displaying a complex phase angle component value for a plurality of frequency components of the complex impedance spectrum.

5. A method in accordance with claim 1 wherein the current pulse has approximately a 10 microamp amplitude and approximately a 0.15 millisecond duration.

6. A method in accordance with claim 5 and further comprising after each current pulse, applying a second, depolarizing pulse having an amplitude and duration substantially equal to the preceding current pulse, but in opposite polarity.

* * * * *